United States Patent
Ichikawa et al.

(10) Patent No.: US 10,799,532 B2
(45) Date of Patent: Oct. 13, 2020

(54) TREATMENT WATER OF LIFESTYLE-RELATED DISEASES AND METHOD OF TREATING THE LIFESTYLE-RELATED DISEASES

(71) Applicants: Yoshio Ichikawa, Yokohama (JP); Taro Shirakawa, Tokyo (JP); Hitoshi Sato, Tokyo (JP)

(72) Inventors: Yoshio Ichikawa, Yokohama (JP); Taro Shirakawa, Tokyo (JP); Hitoshi Sato, Tokyo (JP)

(73) Assignees: Yoshio Ichikawa, Yokohama-shi (JP); Taro Shirakawa, Tokyo (JP); Yasushi Sei, Tokyo (JP)

( * ) Notice: Subject to any disclaimer, the term of this patent is extended or adjusted under 35 U.S.C. 154(b) by 0 days.

(21) Appl. No.: 15/373,731

(22) Filed: Dec. 9, 2016

(65) Prior Publication Data

US 2018/0064756 A1 Mar. 8, 2018

(30) Foreign Application Priority Data

Sep. 2, 2016 (JP) .................................. 2016-171633

(51) Int. Cl.
| | |
|---|---|
| *A61K 33/38* | (2006.01) |
| *A61K 33/242* | (2019.01) |
| *A61K 9/00* | (2006.01) |
| *A61K 9/08* | (2006.01) |
| *A61K 9/10* | (2006.01) |
| *A61K 33/243* | (2019.01) |
| *A61K 33/24* | (2019.01) |

(52) U.S. Cl.
CPC ............ *A61K 33/38* (2013.01); *A61K 9/0095* (2013.01); *A61K 33/24* (2013.01); *A61K 9/08* (2013.01); *A61K 9/10* (2013.01)

(58) Field of Classification Search
CPC .... A61K 33/38; A61K 33/242; A61K 9/0095; A61K 9/08; A61K 9/10
See application file for complete search history.

(56) References Cited

U.S. PATENT DOCUMENTS

| | | | | | |
|---|---|---|---|---|---|
| 5,429,819 | A | * | 7/1995 | Oka | ........................ A01N 59/16 424/400 |
| 6,093,414 | A | * | 7/2000 | Capelli | .................. A01N 59/16 424/405 |

FOREIGN PATENT DOCUMENTS

| | | | |
|---|---|---|---|
| JP | 2004-285166 A | | 10/2004 |
| JP | 2004285166 A | * | 10/2004 |
| JP | 2012-92027 A | | 5/2012 |
| JP | 2015-48348 A | | 3/2015 |
| JP | 2015048348 A | * | 3/2015 |

* cited by examiner

Primary Examiner — Bethany P Barham
Assistant Examiner — Peter Anthopolos
(74) Attorney, Agent, or Firm — Sughrue Mion, PLLC

(57) ABSTRACT

To obtain a lifestyle-related disease therapeutic water which comprises a very small amount of anionized silver, nano-sized gold, and 99.9% or more of water. A lifestyle-related disease therapeutic water comprising with respect to one liter of water (a), 3-15 mg in silver equivalent of thiosulfate silver ion (b), and 0.1-0.5 mg in gold equivalent of colloidal gold (c).

8 Claims, 2 Drawing Sheets
(2 of 2 Drawing Sheet(s) Filed in Color)

[FIG. 1]

TREATMENT WATER OF LIFESTYLE-RELATED DISEASES AND METHOD OF TREATING THE LIFESTYLE-RELATED DISEASES

TECHNICAL FIELD

The present invention relates to therapeutic water to treat or prevent cancer and lifestyle-related diseases such as arteriosclerosis, gastroenteritis, hepatitis, nephritis, diabetes, and the like, and a treating method of the lifestyle-related diseases.

BACKGROUND ART

Ordinary, diseases treatment is a symptomatic therapy by a method using a drug which targets only the found affected area, the therapy causes side effects such as a rash or pain, also causes a deterioration of other organs or immune systems, and further there is a problem such as a risk of recurrence.

The inventors of the present invention have previously proposed an anti-cancer agent comprising (a) water, (b) silver thiosulfate ions and (c) colloidal platinum as main components (Patent Document 1). This anti-cancer agent, by continuing to drink 0.8 to 1.6 liters per day, affects to every cancer cell in the target area, transferred cancer cell, and even unfound small cancer cells and inhibits infiltration and proliferation thereof and to kill the cancer cells, thereby being able to cure perfectly the cancer without recurrence or side effects.

This anti-cancer agent may cure perfectly during the treatment period, even further then, without any recurrence or side effects.

Incidentally, the invention of the prior art reference was recognized to have a novelty and inventive step, and thus granted on Aug. 3, 2016.

PRIOR ART DOCUMENT

Patent Document

[Patent Document 1] JP 2015-48348A

SUMMARY OF THE INVENTION

Problems to be Solved by the Invention

As a result of further studies on the anti-cancer agent above, the present inventors have recognized the following information such that, when using very small amount of colloidal gold instead of the colloidal platinum among a system containing water, colloidal platinum silver complex anion and colloidal platinum, the redox potential was more reduced, a strong reaction like anti-biotics against bacteria, fungi and membranous virus was observed, and a diabetes patient administered insulin for more than 10 years was diagnosed no need of insulin after about five-month administration of the therapeutic water instead of drinking water.

The present invention provides based on the above findings, when drinking 0.5 to 1.5 liters per day of the lifestyle-related disease therapeutic water of the present invention, the therapeutic water circulates the entire body, then works on the target area to treat the lifestyle-related diseases and also works on the other areas if there are any signs, and further compensates for the reduced ability of the various organs associated with aging, and allowing it to become soundness, and thus the object of the present invention is to provide a lifestyle-related disease therapeutic water capable of perfectly curing the affected area.

Means for Solving the Problems

The present invention includes the following (1) to (5).
(1) Lifestyle-related disease therapeutic water comprising the followings;
  (a) with respect to one liter of water,
  (b) 3-15 mg in silver equivalent of thiosulfate silver ion, and
  (c) 0.1-0.5 mg in gold equivalent of colloidal gold.
(2) The lifestyle-related disease therapeutic water according to (1), wherein the water (a) is at least one kind selected from the group consisting of tap water, mineral water, purified water, electrolyzed water and other drinking waters.
(3) The lifestyle-related disease therapeutic water according to (1) or (2), wherein the thiosulfate silver (b) ion is represented by Formula $[Ag(S_2O_3)_2]^{3-}$ and/or Formula $[Ag(S_2O_3)_6]^{11-}$.
(4) The lifestyle-related disease therapeutic water according to any one of (1) to (3), wherein the lifestyle-related disease is at least one kind selected from the group consisting of cancer, diabetes, arteriosclerosis, kidney disease, liver disease, lung disease, heart disease, and gastrointestinal disease.
(5) A method of treating lifestyle-related disease comprising administering 0.5 to 1.5 liters per day of the lifestyle-related disease therapeutic water according to any one of (1) to (4) per oral, by drip, or by catheter.

Advantageous Effective of the Invention

The lifestyle-related disease therapeutic water of the present invention, because of the following capabilities, may cure not only cancer but also lifestyle-related disease such as arteriosclerosis, gastrointestinal disease, liver disease, kidney disease and diabetes without any side effects and keep the entire body healthy, and it may work as prophylactic water for healthy people by drinking 0.5 to 1.5 liters per day in the drinking water sense, thus this is an epoch-making invention which is different from the conventional therapy.

(1) The lifestyle-related disease therapeutic water of the present invention has high permeability and solubility, so lipids, especially harmful lipid peroxides can be gradually dissolved and decomposed, and foreign materials (pollens from the outside, PM, toxins, cancer cells which generate and abnormally proliferate in a body, and abnormal proteins) can be excluded from the body.
(2) The lifestyle-related disease therapeutic water of the present invention has high anti-oxidant power and may inhibit progression of aging.
(3) The lifestyle-related disease therapeutic water of the present invention acts on aerobic bacteria (bad bacteria) and envelope viruses to deactivate them, thereby being able to increase anaerobic bacteria (benefit bacteria).
(4) The lifestyle-related disease therapeutic water of the present invention degrades alcohol and medicines.

The lifestyle-related disease therapeutic water of the present invention having the capabilities (1) to (4) mentioned above can, for example, treat/cure or prevent the following diseases.

Specific examples of the immune activation water of the present invention are as follows.
1) Cancer The lifestyle-related disease therapeutic water of the present invention circulates the entire body, and, by this therapeutic water alone, acts only on not only the target cancer but also every cancer cell (including even unfound small cancer cells) in the body and inhibits infiltration and division/proliferation thereof to kill the cancer cells, and can cure perfectly the cancer without metastasis, recurrence, moreover without acting on normal cells including other organs, and it can normalize the immune system that has been deteriorated in particular by other medicines. This effect is understood that the therapeutic water of the present invention acts on the specific substances produced from the cancer cells and destroys them, then inhibits the division and proliferation of the cancer cells to extinguish them.

2) Diabetes

In diabetes, blood glucose is in a chronically excessive state, and the difficulty of sugar transfer to liver or muscles due to accumulation of visceral fat in blood vessels is a problem rather than the insufficiency of insulin which is secreted from β-cells of the pancreas. If continuing to drink about one liter of the lifestyle-related disease therapeutic water of the present invention, the accumulated visceral fat is gradually decomposed and dissolved, then the blood vessels become clean, thus the sugar is easier to transfer. Even a patient having been administered an insulin injection for more than ten years may stop insulin injections after 4 to 6 months of starting administration of the therapeutic water of the present invention, then blood sugar level and AGE become normal value, respectively.

3) Arteriosclerosis

Arteriosclerosis, where dirt inside of blood vessels (mainly lipids) accumulates so as to harden or narrow the blood vessels, is cured by drinking the therapeutic water of the present invention, so that lipids, especially lipids peroxide caused by the oxidization thereof are decomposed and dissolved, and blood concentration and blood flow are improved, whereby hyperlipidemia, hypertension, stroke (cerebral infarction, cerebral hemorrhage, cerebral thrombosis, etc.), and heart disease (myocardial infarction, angina pectoris, heart failure, etc.) can be treated or prevented.

4) Gastrointestinal Disease

If drinking the therapeutic water of the present invention for 3 to 4 months, aerobic bacteria decrease and anaerobic bacteria increase, and then balance of the intestinal bacteria become excellent, excretion odor disappears and constipation is improved to become free feces. In addition, the state of the small intestine where the immune systems are centralized becomes normal or activated. As a result, peritonitis or colitis can be treated in a short period of time.

In a stomach, the therapeutic water of the present invention eradicates *Helicobacter* or *Helicobacter pylori*, and also gastric ulcer, esophagitis, or chronic gastritis can be treated by cleaning inside of the stomach.

5) Kidney Disease

Kidney diseases progress without subjective symptoms, and it may be too late when noticed. Chronic kidney diseases become worse to kidney failure, followed by causing uremia, and there will be needed artificial dialysis or artificial kidney transplantation.

The therapeutic water of the present invention is to clean the glomerulus, which is the mass of capillaries performing filtration and fractionation of blood, to prevent inflammation, and to normalize gradually the regulation of the blood filtration, the water content, electrolytes, hormones secretion, and the like, whereby it is possible to treat the kidney diseases. Renal artery stenosis is arteriosclerosis.

6) Liver Disease

Liver diseases progress from fatty liver to hepatitis→cirrhosis→liver cancer, and it is caused by obesity, diabetes, drinking too much alcohol, and the like.

The therapeutic water of the present invention decomposes and dissolves excessive lipids and organics so as to activate liver functions especially detoxification function to reduce undue stress on the liver, and may treat the symptoms described above.

Alcohol is decomposed to acetaldehyde acetate carbon dioxide and water, the therapeutic water of the present invention can reduce undue strain on this process.

In particular, chronic hepatitis, of which symptoms can be hardly realized, may be prevented by the therapeutic water of the present invention.

As described above, the lifestyle-related disease therapeutic water of the present invention is different from the conventional symptomatic therapy, it runs through the entire body by drinking this therapeutic water so as to treat not only the target affected area but also an affected area or potential affected area only in this treatment water one, if any, then makes the entire body healthy. Further, because of no side effects, it may be used as a prophylactic water of diseases, and it can be said that it is a revolutionary lifestyle-related disease therapeutic water.

Thus, it cannot be predicted how much health care costs may be reduced due to the lifestyle-related disease therapeutic water of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The upper part of the photograph shows an example using tap water, the bottom part thereof shows an example using the lifestyle-related disease therapeutic water of the present invention.

Figure 2:
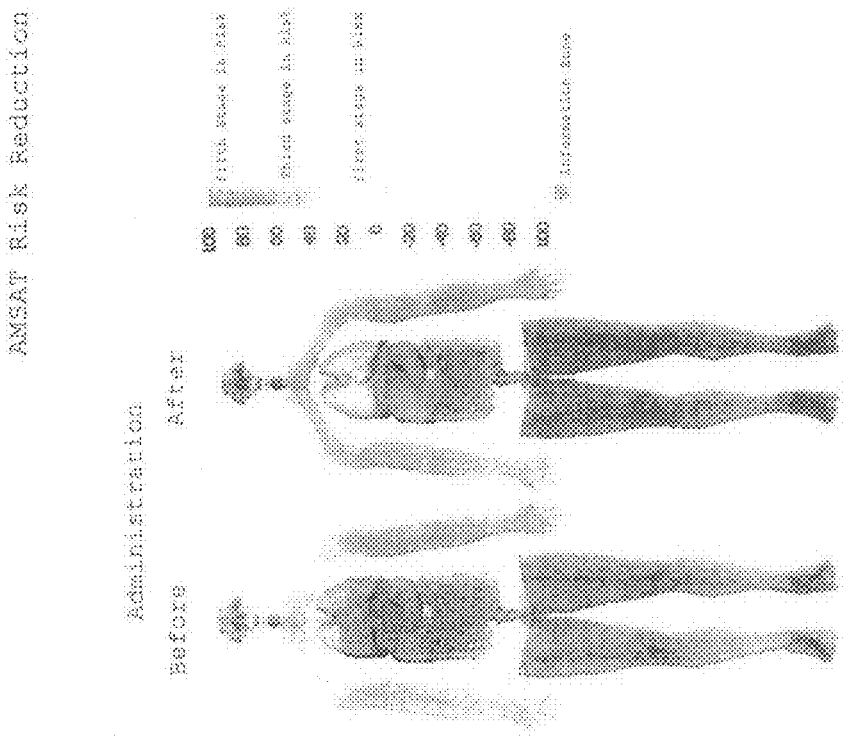

FIG. 2 shows a picture illustrating the results of Test Example 6, which shows the measurement results of the therapeutic water of the present invention according to the AMSAT.

EMBODIMENTS FOR CARRYING OUT THE INVENTION

The lifestyle-related disease therapeutic water of the present invention contains water as a main component and to which silver thiosulfate ions and colloidal gold are added.

Therefore, the therapeutic water of the present invention contains a very small amount of silver negative ions and gold nanoparticles with catalytic activity. It contains 99.9% or more of water, and when drinking, it demonstrates a performance as therapeutic water for various lifestyle-related diseases as described below circulating through the entire body without accumulation.

(1) Dissolved oxygen ($O_2$) in the therapeutic water, which is chemically adsorbed to the silver component contained in the water, becomes singlet oxygen ($^1O_2$), and the energy of 22 Kcal/mol generated by this reaction breaks the hydrogen bonds of the water molecules to make the cluster (water molecules assembly) smaller, whereby the permeability and solubility of the therapeutic water becomes higher, thereby obtaining the cleaning ability to gradually dissolve or decompose lipids, especially lipid peroxides, and also the electrical conductivity and thermal conductivity thereof become high.

(2) The therapeutic water of the present invention scavenges free radicals ($O^-{}_2$, etc.) and inhibits oxidation progress.

(3) The therapeutic water of the present invention eradicates aerobic bacteria and deactivates envelope viruses.

(4) The therapeutic water of the present invention degrades alcohol and medicines.

(5) The therapeutic water of the present invention is extensively safe and has no side effects. Thus the therapeutic water of the present invention may also be consumed by healthy people to prevent lifestyle-related diseases.

Since the lifestyle-related disease therapeutic water of the present invention has the effects mentioned above, by drinking 0.5 to 1.5 liters per day of the therapeutic water, the therapeutic water circulates the entire body, then works on the target area to cure and also works on the other areas if there is an area showing signs of diseases, and further supports disability of organs due to aging and treat them, thus recovers and maintain a healthy body.

The lifestyle-related disease therapeutic water includes, with respect to one liter of water (a), 3-15 mg in silver equivalent of thiosulfate silver ion (b) and 0.1-0.5 mg in gold equivalent of colloidal gold (c).

The lifestyle-related disease therapeutic water of the present invention is described below for each component.

(a) Water

Water (a) is at least one kind selected from the group consisting of tap water, mineral water, purified water, electrolyzed water and other drinking waters. The water (a) may include component (b) and component (c) which constitutes the therapeutic water of the present invention, thus total amount of the water in the therapeutic water of the present invention is not less than 99.9% when including water as component (a).

(b) Thiosulfate Silver Ion

Thiosulfate silver ion (b) in thiosulfate silver is used in the lifestyle-related disease therapeutic water of the present invention based on the following capabilities.

(1) Based on the high permeability and solubility thereof, lipids, especially harmful lipid peroxides can be gradually dissolved, decomposed and excluded from the body. This high cleaning power excludes foreign materials (pollens from the outside, PM, toxins, cancer cells which generate and abnormally proliferate in a body, and abnormal proteins) and also decomposes alcohol and chemicals.

(2) Free radicals in a body are scavenged, and oxidation progress is inhibited.

(3) Aerobic bacteria are eradicated and anaerobic bacteria are increased. Envelope viruses consisting mostly of lipids are deactivated.

(4) Silver thiosulfate ions are anionic, and are not accumulated or deposited in a body, do not react with salts, and circulate in a body and reach the affected area to treat.

Thiosulfate silver ion (b) may be, but not limited, prepared by the following method.

(1) To silver nitrate solution is added sodium hydroxide solution to obtain blackish brown precipitation. The supernatant is removed and washed fully, thereafter sodium thiosulfate solution is added thereto to dissolve the precipitation, and to give pale clear yellow solution of thiosulfate silver ion.

(2) To commercially available silver oxide is added sodium thiosulfate solution, and the silver oxide is melted to obtain silver thiosulfate ion solution.

Thiosulfate silver ion in component (b) may be preferably represent Formula $[Ag(S_2O_3)_2]^{3-}$ and/or Formula $[Ag(S_2O_3)_6]^{11-}$.

If thiosulfate ion $S_2O_3{}^{2-}$ concentration is low in the methods above, the Formula is $[Ag(S_2O_3)_2]^{3-}$, and if it is high, the Formula is $[Ag(S_2O_3)_6]^{11-}$.

Silver thiosulfate ion (b), may be 3-15 mg in silver equivalent (57-285 mg in solid equivalent) with respect to one liter of water (a), preferably 4-12 mg in silver equivalent. If it is below 3 mg, the power to inhibit infiltration/proliferation of cancer cell or to kill aerobic bacteria, fungi and virus effect is not enough, and thus it is difficult to cure the lifestyle-related disease. If the ion is more than 15 mg, inhibitory effects of the therapeutic waters to the lifestyle-related diseases such as anti-cancer, anti-aerobic bacteria, anti-fungus or anti-virus effects become constant, thus it is not economical.

Colloidal Gold (c)

Colloidal gold (c) contains gold having average primary diameter of about 10 nm, and is dispersed and stabilized in water. In the present invention, it is considered that the colloidal gold (c) can enhance the capability of the lifestyle-related disease therapeutic water by catalytic activity of the gold nanoparticles thereof based on the most of the capability of the combined component (b).

That is, it is considered that the effect of the colloidal gold (c) is increased in combination with the component (b) and the function which inhibits the infiltration and growth of cancer cells at any site to extinguish them is increased. Further, the colloidal gold (c), by using in combination with the component (b), can kill aerobic bacteria, fungi and viruses.

Incidentally, since most of the therapeutic water of the present invention is water, aqueous colloidal gold is used as the colloidal gold (c).

The colloidal gold (c) used herein can significantly reduce a redox potential of the obtained inorganic anti-biotics in combination with the component (b) comparing with an aqueous colloidal platinum, thus as anti-aerobic bacterial, anti-fungal, anti-viral, or anti-cancer agents, it is effective with a significant difference from the Patent Document 1 mentioned above.

A number of methods to produce the colloidal gold (c) have been known (for example, JP 57-43125B, JP 59-120249B, and JP H9-225317A, JP H10-176207A, JP 2001-79382A, JP 2001-122723A), one skilled in the art can readily prepare the gold microparticles by referring to these methods. For example, as a method of producing the gold microparticles, chemical methods called precipitation method or metal salt reduction method or physical methods called combustion method may be used. As the component (c) of the present invention, the gold microparticles prepared by any of the methods may be used, it is preferred to use the gold microparticles prepared by the metal salt reduction method from the aspect of easiness and quality.

In the metal salt reduction reaction method, for example, the gold microparticles may be produced by preparing an aqueous solution or an organic solvent solution of water-soluble or organic solvent-soluble gold (salt) or gold complexes, adding a water soluble polymer to the obtained solution, then adjusting pH of the obtained solution to 9~11, and reducing by heat reflux under an inert atmosphere. The water-soluble or organic solvent-soluble gold salt includes, but not limited to, for example, acetates, chlorides, sulfates, nitrates, sulfonates, phosphates, and the like, also a combination thereof can also be used.

A specific example of the production method of colloidal gold (c) used for the present invention is shown below.

(1) One gram of tetra chloroauric (III) acid is dissolved in pure water to prepare 500 g of aqueous solution (0.2% chloroauric acid aqueous solution).

(2) Pure water is added to 13.13 g of potassium hydroxide (KOH) to prepare 1,000 g of aqueous solution, then 900 g of the obtained solution and 100 g of 35% formalin solution is mixed to prepare a potassium hydroxide-formalin mixture.

(3) To 100 g of 0.2% chloroauric acid aqueous solution obtained in the above (1), 900 g of pure water is added to prepare 1,000 g of solution.

(4) To 1,000 g of 0.02% chloroauric acid aqueous solution, 40 g of potassium hydroxide-formalin mixture solution obtained in the above (2) is slowly added to prepare a purple-red gold colloid.

The obtained gold colloid includes approx. 92 mg/1 kg of gold.

Incidentally, the therapeutic water of the present invention may include, if necessary, aqueous colloidal platinum in addition to the components (a) to (c).

The preparation method of the therapeutic water of the present invention includes adding the components (b) and (c) to the component (a), then stirring and mixing them. If necessary, water (a) may further be added thereto, followed stirring and mixing.

In the lifestyle-related diseases therapeutic water of the present invention, it can be said that water (a) is modified by adding the component (b), and the component (c) to become anti-aerobic bacteria, anti-fungal, anti-virus, and anti-cancer water. Thus, it is necessary to circulate the water through the entire body by drinking 0.5 to 1.5 liters per day of the therapeutic water of the present invention. The therapeutic water can be administered by drinking everyday like normal drinking water.

This improved water is excellent in anti-oxidant effect (reducibility), lipid degradability, anti-bacterial effect (against only aerobactor), anti-virus activity (against only membranous virus), anti-envelope virus activity, permeability, solubility and cleaning ability, it does not act on a normal cell, and acts only on the target area of the lifestyle-related disease without side effects, so that it may be considered as an extremely safe therapeutic water, and also believed to be a drinking water, which cleans up every organ, inhibits internal body oxidation, provides good balance of the bacteria in the intestine, and regains true healthy body.

EXAMPLES

The present invention will hereinafter be described further specifically with reference to examples, but the scope of the present invention is not limited to those examples so far as it does not exceed the scope of the claims.

Example 1 (Preparation of Therapeutic Water)

To 1,000 g of pure water (a), 75 mg (approx. 3.46 mg in silver equivalent) of the below-mentioned component (b) and 1.5 g (approx. 0.14 mg in gold equivalent) of the below-mentioned component (c) was added to prepare the therapeutic water of the present invention.

(a) pure water 1,000 g
(b) silver thiosulfate ion 75 mg (approx. 3.46 mg in silver equivalent)
(c) gold colloid 1.5 g (approx. 0.14 mg in gold equivalent)

Example 2

To 1,000 g of pure water (a), 132 mg (approx. 6.98 mg in silver equivalent) of the below-mentioned component (b) and 3 g (approx. 0.27 mg in gold equivalent) of the below-mentioned component (c) was added to prepare the therapeutic water of the present invention.

(a) pure water 1,000 g
(b) silver thiosulfate ion 132 mg (approx. 6.98 mg in silver equivalent)
(c) gold colloid 3 g (approx. 0.27 mg in gold equivalent)

Example 3

To 1,000 g of pure water (a), 226 mg (approx. 11.95 mg in silver equivalent) of the below-mentioned component (b) and 4.5 g (approx. 0.41 mg in gold equivalent) of the below-mentioned component (c) was added to prepare the therapeutic water of the present invention.

(a) pure water 1,000 g
(b) silver thiosulfate ion 226 mg (approx. 11.95 mg in silver equivalent)
(c) gold colloid 4.5 g (approx. 0.41 mg in gold equivalent)

The component (b) and component (c) was prepared as follows.

<Preparation of the Component (b) (Silver Thiosulfate)>

To 1 g of silver nitrate aqueous solution, 5% sodium hydroxide solution was added to prepare a blackish brown precipitation, then supernatant of the obtained was removed, the precipitation was washed with pure water three times and to obtain silver oxide.

To the obtained silver oxide, 4 g of anhydrous sodium thiosulfate was added and adjusted the concentration by adding pure water to prepare 10 g of silver thiosulfate ion (approx. 529 mg in silver equivalent).

<Preparation of the Component (c) (Aqueous Colloidal Gold)>

One gram of chloroauric acid ($HAuCl_4 \cdot 4H_2O$), 13.14 g of potassium hydroxide (KOH), 100 g of 35% formalin (HCHO), and pure water was used to prepare colloidal gold in the following manner.

1) One gram of chloroauric acid was dissolved in pure water to prepare 500 g of 0.2% chloroauric acid aqueous solution, and then 900 g of pure water was added to the 100 g of the obtained solution to furnish 1,000 g of 0.02% chloroauric acid aqueous solution.

2) In pure water, 13.14 g of potassium hydroxide was dissolved to prepare 1,000 g of 0.2% potassium hydroxide aqueous solution, and thereafter a mixture of 900 g of the obtained solution and 100 g of 35% formalin solution was prepared.

3) To 1,000 g of 0.02% chloroauric acid aqueous solution obtained in the above 1), 40 g of potassium hydroxide-formalin mixture solution obtained in the above 2) was slowly added to prepare a purple-red gold colloid. The obtained gold colloid includes approx. 92 mg/1,000 g of gold.

Details of the therapeutic water in Examples 1 to 3 are shown in Table 1.

TABLE 1

|  | Pure water | Ag thiosulfate ion | (Ag equivalent) | Gold colloid | (Gold equivalent) | Total |
|---|---|---|---|---|---|---|
| Example 1 | 1,000 g | 75 mg | ≈3.46 mg | 1.5 g | ≈0.14 mg | ≈1,001.6 g |
| Example 2 | 1,000 g | 132 mg | ≈6.98 mg | 3 g | ≈0.27 mg | ≈1,003.1 g |
| Example 3 | 1,000 g | 226 mg | ≈11.95 mg | 4.5 | ≈0.41 mg | ≈1,004.7 g |

Test Example 1

To determine anti-bacterial activity of the lifestyle-related diseases therapeutic water of the present invention, aerobactor *Escherichia coli* (O-157:H7) and methicillin-resistant *Staphylococcus aureus* (MRSA) were respectively added to the therapeutic water of Example 2 [Sample (2)], then counted the number of viable bacteria after 1 hour and 3 hours at room temperature. The result is shown in Table 2.

In Table 2, the control refers pure water used for the preparation of Sample (2). "<10," refers to "no detection."

TABLE 2

| Test bacteria | Test solution | Viable bacteria count (/ml) | | |
|---|---|---|---|---|
| | | Initial | After 1 hour | After 3 hours |
| *Escherichia coli* | Sample (2) | $7.4 \times 10^5$ | <10 | <10 |
| (O-157:H7) | Control | $7.4 \times 10^5$ | $2.4 \times 10^5$ | $2.8 \times 10^5$ |
| MRSA | Sample (2) | $7.1 \times 10^5$ | <10 | <10 |
| | Control | $7.1 \times 10^5$ | $1.3 \times 10^5$ | $3.1 \times 10^5$ |

Test Example 2

Liquid including yeast fungus, which is anaerobes bacteria (yeast fungus with no addition of bacteria) was added to the therapeutic water (1) obtained in Example 1 [Sample (1)] and the therapeutic water (2) obtained in Example 2 [Sample (2)], then counted viable bacteria after 24 hours, 38 hours, and 72 hours at room temperature.

As a control, boiled tap water was used. The result is shown in Table 3.

Table 3 shows that the therapeutic water of the present invention worked for growth of yeast fungus comparing with conventional tap water.

TABLE 3

| | Viable bacteria count (/ml) | | | |
|---|---|---|---|---|
| Test solution | Initial | After 24 hours | After 48 hours | After 72 hours |
| Sample (1) | $3.1 \times 10^5$ | $3.8 \times 10^5$ | $4.6 \times 10^5$ | $7.3 \times 10^5$ |
| Sample (2) | $3.1 \times 10^5$ | $3.7 \times 10^5$ | $4.6 \times 10^5$ | $7.2 \times 10^5$ |
| Control | $3.1 \times 10^5$ | $3.2 \times 10^5$ | $3.8 \times 10^5$ | $4.8 \times 10^5$ |

Test Example 3

By using the therapeutic water (1) and (2) obtained in Example, an oxidation-reduction potential was measured. As a control, commercially available mineral water (1) and mineral water (2) were used. The results are shown in Table 4.

Table 4 proved that pH of the added water with the addition of therapeutic water of the present invention is not different from the mineral water which is raw water, the oxidation-reduction potential decreases significantly, and it has been a reduced water state.

TABLE 4

| | Water temperature (° C.) | pH | Oxidation-reduction potential (mV) |
|---|---|---|---|
| Mineral water (1) | 22.5 | 8.1 | 395 |
| Therapeutic water (1) | 22.5 | 8.1 | 112 |
| Therapeutic water (2) | 22.5 | 8.1 | 105 |
| Mineral water (2) | 22.2 | 7.2 | 423 |
| Therapeutic water (1) | 22.2 | 7.2 | 181 |
| Therapeutic water (2) | 22.2 | 7.2 | 161 |

Test Example 4

To determine clusters (aggregation state of water) of the lifestyle-related diseases therapeutic water of the present invention, by using the therapeutic water (1) of Example 1, a line width (Hz) obtained by digitizing the spectra detected by nuclear magnetic resonance (NMR) was measured.

<Measurement Conditions>
Measurement nuclide $^{17}O$ (oxygen-17)
Use equipment manufactured by JEOL Ltd., JNM-EX270
Measurement temperature 20° C.

<Results>
The line width (half width) of the sample [therapeutic water (1)] was as follows.
Mineral water (1) (see the above) 85.7 Hz
Therapeutic water (1) (Example 1) 61.2 Hz The half-width refers one-half width (thickness) of the peak height and the unit is Hz (Hertz).

The narrower line width, that is the narrower half-width, shows water with small cluster, in which an osmotic pressure and solvency is high, also an electrical conductivity and thermal conductivity is high.

In general, a line width of water is 140-150 Hz in pure water, 90-140 Hz in tap water, and 80-90 Hz in mineral water, thus it is understood that the therapeutic water (1) of the present invention has smaller water cluster.

Test Example 5

An anti-oxidant property and a lipolytic/solubility of the therapeutic water (2) prepared in Example 2 of the present invention were determined.

First, two slices (4 cm×3 cm×about 5 mm (thickness) block) of commercially available butter (manufactured by Snow Brand Milk Products Co., Ltd.) were prepared. Then, two glass containers were prepared, and 350 ml of mineral water alone (pH 7.3) and 350 ml of therapeutic water (2) was respectively poured into one of the two glass containers, and the butter slices were placed in the glass container one for each, a glass plate was put on the top of the containers and observed for 28 days at room temperature.

Figure 1:
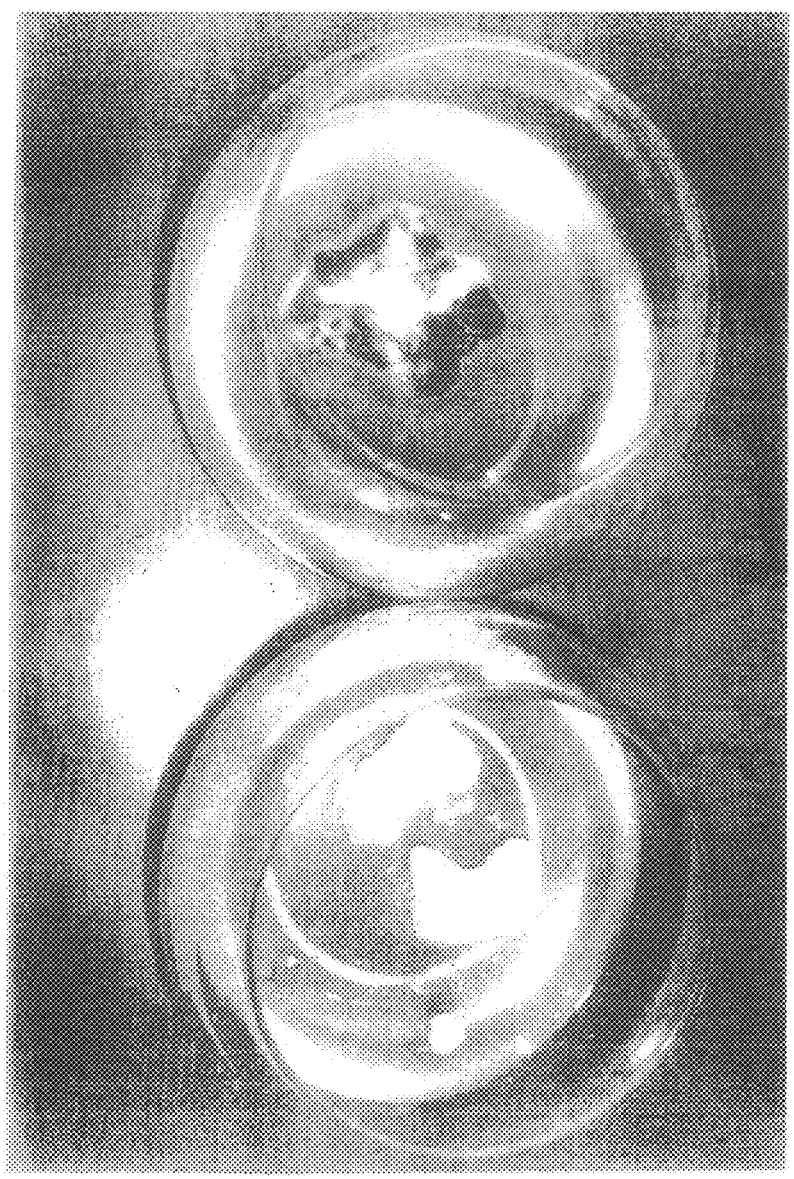
FIG. 1 shows a photograph depicting the results of testing anti-oxidant and lipolytic properties of butter in Test Example 5, using the therapeutic water of the present invention.

The results are shown in FIG. 1. The surface of the butter is hardened and darkened by oxidation in the container with the mineral water alone.

In contrast, in the container with the lifestyle-related diseases therapeutic water of the present invention (2), no oxidation is observed, that means degradation and dissolution of the butter has proceeded.

Test Example 6

With a device "medical equipment certification number 221AIBZX00020000 (general name: treatment inspection search measuring instrument AMSAT "automated skin resistance measurement system") made in Germany," risks in every organ of the male having a higher blood sugar value (age 49, blood sugar value 142 mg/dL), who was daily administered one liter/day of the lifestyle-related diseases therapeutic water (1) (Example 1) of the present invention for three months, before and after three months (reference blood sugar value 116 mg/dL) of administering were measured. The results are shown in FIG. 2.

FIG. 2 shows that the risks in 15 organs have been significantly decreased in only 3 months. This data shows that one disease affects the entire body, and it is possible not only to cure the affected area, but also reduce the risks of other organs or normalize them to maintain healthy body by systemic circulation as of the lifestyle-related diseases therapeutic water of the present invention.

Test Example 7

Anti-proliferative activity against cancer cell of the lifestyle-related diseases therapeutic water was determined.

On the day before the test, breast cancer cells MCF-7 (2,000 cells/well) and lung cancer cells A549 (500 cells/well) were disseminated to 96 well plate, respectively.

On the day of experimentation, the therapeutic water (2) and the therapeutic water (3) obtained in Examples were added, respectively, 150 μl to each well.

Thereafter, at room temperature, cell culture was performed for 6 days. After finishing the cell culture, survival rate of the cell was determined according to MTT method prepared in Example 2 by measuring the Absorbance at 570 nm and 620 nm. As a control, 0 day cell count was determined according to the MTT method. Incidentally, the therapeutic water (2) and the therapeutic water (3) were measured 3 times.

<Test Results>

It was observed that the therapeutic water (2) and the therapeutic water (3) inhibited cell proliferation (complete) in MCF7 and A549 cells.

INDUSTRIAL APPLICABILITY

The present invention provides the therapeutic water which comprises a very small amount of anionized silver and nanosized gold and 99.9% or more of water. By continuing to drink 0.5 to 1.5 liter of the therapeutic water orally everyday like drinking water, the therapeutic water circulates the entire body and acts only on every cancer cell, aerobic bacteria, fungi, and membranous virus so as to inhibit infiltration and proliferation thereof and to kill the cancer cells, and the therapeutic water does not act on a normal cell totally, but may inhibit internal body oxidation and degrade lipid peroxide, and may inactivate aerobactor, fungi and membranous virus to cure with no side effects, further it may clean up every organ including blood vessels, inhibit internal body oxidation, provide good balance of the bacteria in the intestine, and thus regain a healthy body, so it is also useful as healthy water.

The present application claims priority from Japanese Patent Application No. 2016-171633 filed Sep. 2, 2016, the disclosure of which is incorporated herein by reference.

What is claimed is:

1. A lifestyle-related disease therapeutic water comprising the following:
   (a) with respect to one liter of water,
   (b) 3-15 mg in silver equivalent of thiosulfate silver ion, and
   (c) 0.1-0.5 mg in gold equivalent of colloidal gold, wherein the lifestyle-related disease therapeutic water does not contain colloidal platinum.

2. The lifestyle-related disease therapeutic water according to claim 1, wherein (a) the water is at least one kind selected from the group consisting of tap water, mineral water, purified water, electrolyzed water and other drinking waters.

3. The lifestyle-related disease therapeutic water according to claim 1, wherein (b) the thiosulfate silver ion is represented by Formula $[Ag(S_2O_3)_2]^{3-}$ and/or Formula $[Ag(S_2O_3)_6]^{11-}$.

4. The lifestyle-related disease therapeutic water according to claim 1, wherein the lifestyle-related disease is at least one kind selected from the group consisting of cancer, diabetes, arteriosclerosis, kidney disease, liver disease, lung disease, heart disease, and gastrointestinal disease.

5. The lifestyle-related disease therapeutic water according to claim 2, wherein (b) the thiosulfate silver ion is represented by Formula $[Ag(S_2O_3)_2]^{3-}$ and/or Formula $[Ag(S_2O_3)_6]^{11-}$.

6. The lifestyle-related disease therapeutic water according to claim 2, wherein the lifestyle-related disease is at least one kind selected from the group consisting of cancer, diabetes, arteriosclerosis, kidney disease, liver disease, lung disease, heart disease, and gastrointestinal disease.

7. The lifestyle-related disease therapeutic water according to claim 3, wherein the lifestyle-related disease is at least one kind selected from the group consisting of cancer, diabetes, arteriosclerosis, kidney disease, liver disease, lung disease, heart disease, and gastrointestinal disease.

8. The lifestyle-related disease therapeutic water according to claim 5, wherein the lifestyle-related disease is at least one kind selected from the group consisting of cancer, diabetes, arteriosclerosis, kidney disease, liver disease, lung disease, heart disease, and gastrointestinal disease.

* * * * *